(12) United States Patent
Yohe et al.

(10) Patent No.: US 8,376,119 B2
(45) Date of Patent: Feb. 19, 2013

(54) APPARATUS AND METHOD FOR INSPECTING AND ORIENTING ARTICLES

(75) Inventors: Peter D. Yohe, Bloomsburg, PA (US); Ronald H. Cordingly, Berwick, PA (US); Thomas M. Zurewich, Orangeville, PA (US)

(73) Assignee: Dyco, Inc., Bloomsburg, PA (US)

( * ) Notice: Subject to any disclaimer, the term of this patent is extended or adjusted under 35 U.S.C. 154(b) by 362 days.

(21) Appl. No.: 12/825,161

(22) Filed: Jun. 28, 2010

(65) Prior Publication Data

US 2011/0315509 A1    Dec. 29, 2011

(51) Int. Cl.
*B65G 43/08* (2006.01)
(52) U.S. Cl. ......... 198/395; 198/401; 198/406; 198/561
(58) Field of Classification Search ............. 198/341.03–341.05, 395, 401, 198/406, 407, 561, 607; 209/522–529, 538
See application file for complete search history.

(56) References Cited

U.S. PATENT DOCUMENTS

| | | | |
|---|---|---|---|
| 4,257,516 A | 3/1981 | Ionescu | |
| 4,500,203 A | 2/1985 | Bieringer | |
| 4,691,231 A | 9/1987 | Fitzmorris et al. | |
| 4,717,027 A * | 1/1988 | Laure et al. | 209/620 |
| 4,825,995 A | 5/1989 | Nalbach | |
| 4,915,237 A * | 4/1990 | Chang et al. | 209/524 |
| 5,236,077 A * | 8/1993 | Hoppmann et al. | 198/380 |
| 5,314,055 A * | 5/1994 | Gordon | 198/395 |
| 5,591,462 A * | 1/1997 | Darling et al. | 425/173 |
| 5,934,440 A * | 8/1999 | Kroghrud | 194/212 |
| 6,860,379 B2 * | 3/2005 | Matsuda et al. | 198/550.1 |
| 7,270,229 B2 | 9/2007 | Perazzo et al. | |

* cited by examiner

*Primary Examiner* — Mark A Deuble
(74) *Attorney, Agent, or Firm* — McNees Wallace & Nurick LLC (57) ABSTRACT

The present invention relates to an apparatus and methods for inspecting and orienting manufactured articles. The apparatus and method include recirculating inspected articles to the inspection station for additional processing.

19 Claims, 8 Drawing Sheets

APPARATUS AND METHOD FOR INSPECTING AND ORIENTING ARTICLES

FIELD OF THE INVENTION

The present invention generally relates to article inspection and handling. The present invention more particularly relates to a method and apparatus for automatically visually inspecting and orienting blow-molded containers.

BACKGROUND

In the manufacture and packaging of blow-molded articles, such as hollow plastic containers or bottles, it is necessary that the containers be of uniform size and shape, and be free of defect. Additionally, scrap material from the manufacturing process may need to be separated from the blow molded articles before the blow-molded articles are packaged or further processed.

In the manufacture of blow molded bottles, the blow-molding operation results in th formation of "tail" at the closed end of the bottle, which tail must be snapped of, this generally being accomplished during removal of the bottle from the blow-molding machine. The blow-molding operation also results in the formation of a ringlike collar (also known as a "moil") around the opening to the bottle, which moil is cut off from the molded bottle substantially upon completion of the molding operation. The blow-molded bottles, tails and moils are then generally discharged from the blow-molding machine, and must be later separated before further processing.

Further processing may include inspecting and orienting of the blow-molded bottles prior to filling, packaging, or other bottle handling operation. The blow-molded bottles may be fed to an inspection device where the bottles may be manually or automatically inspected. The bottles may also be fed to an unscrambling device where they are unscrambled.

The use of a large number of varying-sized articles to orient and/or package poses a particular problem to the manufacturing and packaging industries because they oftentimes are designed for a fixed size article. Thus, in order to change from one size container to another, for example, the various machinery, tooling, parts (such as guide arms, unscrambler bowl, etc.), had to be "changed out" before the machinery could accommodate another size. This change over not only results in additional costs, but also results in lost revenue due to down time.

Accordingly, there is a need in the industry for a cost effective and operationally efficient inspection and alignment apparatus and method for blow molded articles.

SUMMARY OF THE INVENTION

An objective of the present invention is to provide method and apparatus for inspecting and orienting manufactured articles, such as blow-molded containers.

According to one aspect of the present invention, an apparatus is disclosed that includes an article receiving station, a waste separation station, an inspection station, and a conveyance device for transporting articles between the article receiving station, the waste separation station, and the inspection station. The conveyance device recirculates articles not removed from inspection station back to the article receiving station.

Another aspect of the present invention is to provide an article inspecting and orienting apparatus including an article receiving station, a waste separation station, an article leveling station, an inspection station, and a conveyance device for transporting articles between the article receiving station, the waste separation station, and the inspection station. The conveyance device recirculates articles not removed from inspection station back to the article receiving station.

Another aspect of the present invention is to provide a method of inspecting and orienting a plurality of articles including the steps of receiving a plurality of articles from a manufacturing process at a receiving station, separating manufacturing waste from the plurality of articles, providing the plurality of articles to an inspection station, inspecting the received plurality of articles, removing defective articles from the plurality of articles that fail inspection, orienting acceptable articles from the plurality of articles that pass inspection, and recirculating remaining articles that pass through the inspection station to the receiving station.

BRIEF DESCRIPTION OF THE DRAWINGS

Referring now to the figures, which are exemplary embodiments, and wherein the like elements are numbered alike.

DETAILED DESCRIPTION

Specific embodiments of systems and processes for inspecting and orienting articles according to the invention are described below with reference to the drawings.

FIGS. 1-4 illustrate an apparatus 100 for inspecting and orienting articles 105 according to an embodiment of the disclosure. Referring to FIGS. 1-4, the apparatus 100 includes a housing 110 having a generally rectangular footprint. In another embodiment, the housing 110 may have a rectangular, square, or other footprint geometry capable of housing inspection and orienting components of the apparatus 100.

The apparatus 100 further includes a conveyance device 120 for conveying articles 105 between various stations within the apparatus 100. In this embodiment, the conveyance device 120 includes a first section 122, a second section 124, and a third section 126. In another embodiment, the conveyance device 120 may include one or more sections.

In this exemplary embodiment, the first, second and third sections 122, 124, 126 are belt conveyors. The first, second, and third sections 122, 124, 126 include a conveyor or conveyor belt 140 having an upward facing belt surface 142 and a drive (not shown) for causing the conveyor belt system 140 to move. The conveyor belt 140 of the different sections have different lengths. In another embodiment, the conveyor 140 of one or more of the sections may have the same length.

The first section 122 further includes a plurality of evenly spaced support dividers 123. The support dividers 123 are structures that are at least partially protruding or above the belt surface 142. The support dividers 123 may support, divide, and/or stabilize articles 105 on the belt surface 142 as the articles are moved up an inclined conveyor belt. In another embodiment, one or all of the first, second, and third sections 122, 124, 126 may be or may include a belt conveyor, matt top conveyor, roller conveyor, chute or slide or other similar article transport.

The apparatus 100 further includes an article receiving station 200 configured to receive articles 105 from an article source (not shown). The article receiving station 200 may be a chute, opening or other receiving area for receiving articles 105 onto the first section 122 from an article source. The article source may be a chute, belt, conveyor, manual feed, or other similar article providing device or means for providing and/or loading articles onto the first section 122. In addition to articles 105, the first section 122 may receive manufacturing waste 106. The manufacturing waste 106 may include, but is not limited to tails 107 and moils 108. The apparatus 100 may further include a second article receiving station 201 for receiving articles 105 from an article source. The second article receiving station 201 is an opening in the housing 110 that allows for articles 105 to be placed, fed or otherwise received on the second section 124. In yet another embodiment, the apparatus 100 may include one or more article receiving stations positioned at different locations on the first section 122. The first section 122 transports the articles 105 and any manufacturing waste 106 from the article receiving station 200 to a waste separation station 300. At the waste separation station 300, manufacturing waste 106 is separated from articles 105.

In this exemplary embodiment, the waste separation station 300 includes an open bar grid 310 configured to support articles 105 while allowing manufacturing waste 106 to pass through to a waste discharge chute 320. The waste separation station 300 may include a transverse grid of ¼ inch rods 302 that form a screen and angled chute. In one embodiment, the rods 302 may be ¼ inch rods. In another embodiment, the rods 302 may have a diameter between about ⅛ inch and about ½ inch. In another embodiment, the rods 302 are of a diameter selected to support the articles 105 while passing manufacturing waste 106 therethrough. The rods 302 are perpendicular to the movement of the conveyor belt 140, and thereby orient the manufacturing waste 106, especially the tails 107, with the rods 302 to effectively remove the manufacturing waste 106, especially the tails 107, by passing the manufacturing waste 106 through the space between the rods 302. The waste discharge chute 320 discharges manufacturing waste 106 from the apparatus 100. In another embodiment, the waste separation station may include a grid, screen, automated waste removal device, such as, but not limited to a robotic visually guided arm, vacuum removal system or other devices configured to remove manufacturing waste 106 from the articles 105.

The articles 105 are transported from the waste separation station 300 to the second section 124. In this exemplary embodiment, the articles 105 are transported from the waste separation station 300 to the second station by gravity feed from the angle of the chute formed by the rods 302. In another embodiment, the articles 105 may be transported from the waste separation station 300 to the second section 124 by a conveyor, scraper, bar, chute or other similar transport device.

Figure 5:
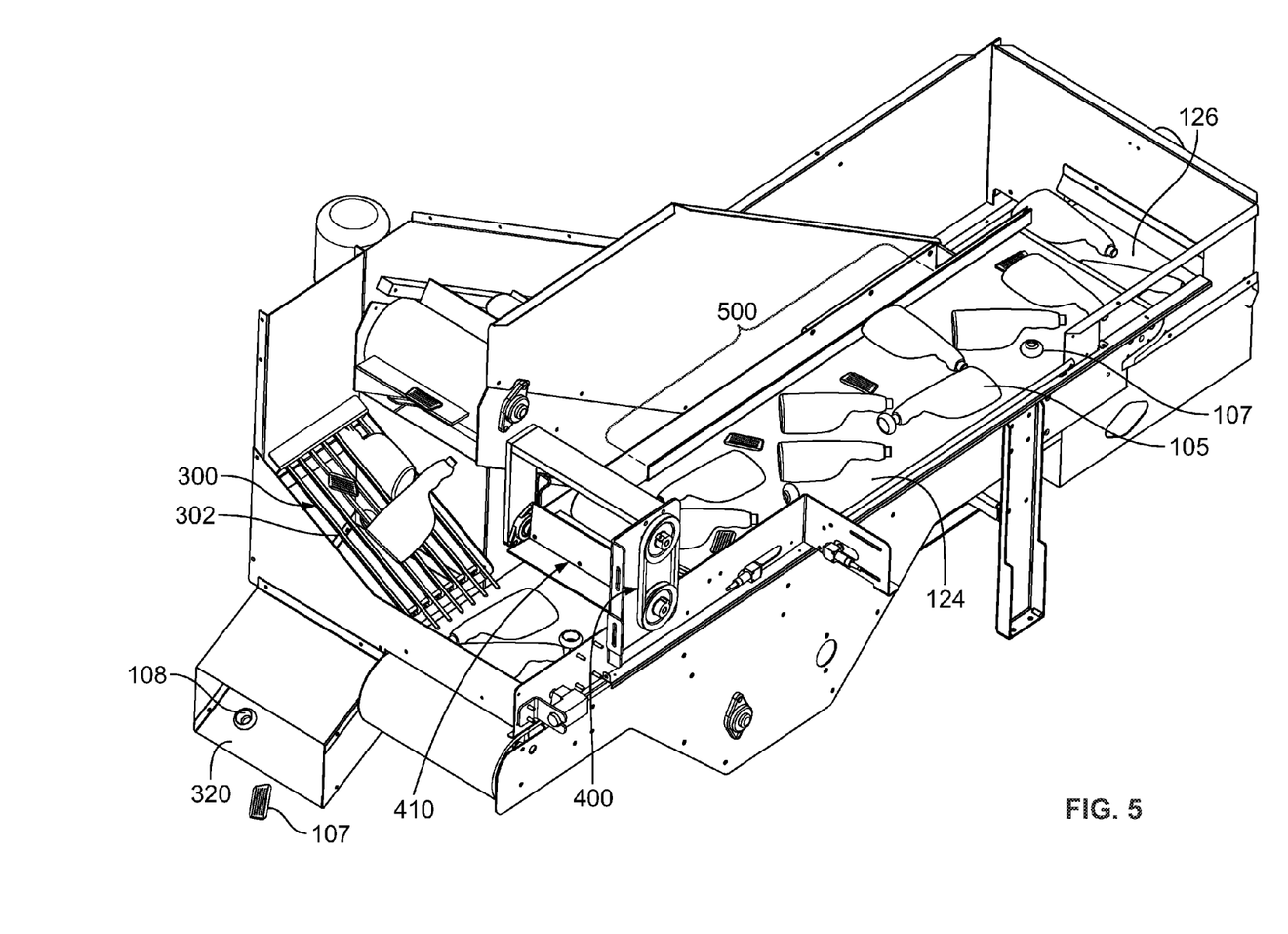
FIG. 5 illustrates a perspective view of the second section of the conveyance device according to an embodiment of the disclosure.
Figure 6:
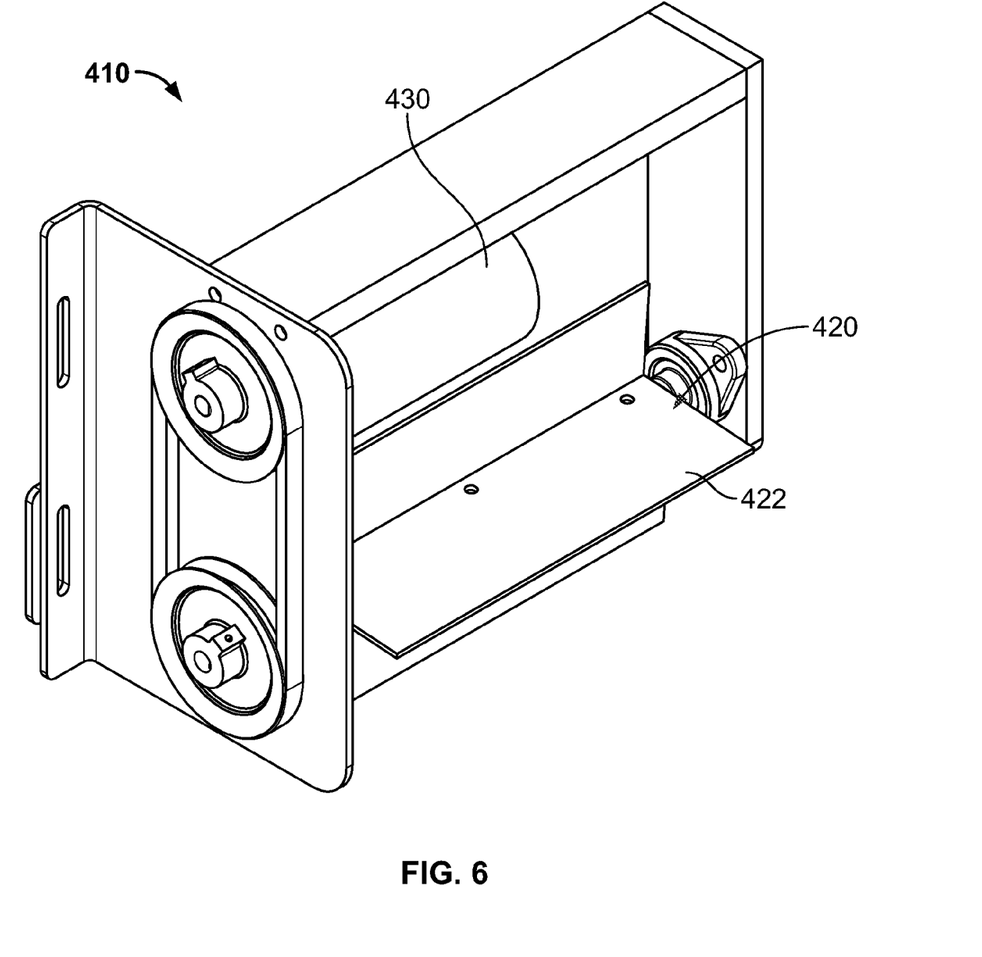
FIG. 6 illustrates a perspective view of the leveling device according to an embodiment of the disclosure.

The articles 105 are transported by the second section 124 to an article leveling station 400. The article leveling station 400 will be described with reference to FIGS. 5 and 6. The article leveling station 400 includes a leveling device 410. The article leveling device 410 includes a paddle wheel 420. The leveling device 410 further includes a motor 430 configured to drive the paddle wheel 420. In this exemplary embodiment, the paddle wheel 420 include four paddles 422. In another embodiment, the paddle wheel 420 may include one or more paddles 422. The paddle wheel 420 is driven by the motor 430 to rotate above the conveyor belt 140 to level the articles over the conveyor belt 140. In other words, the article leveling station orients the articles 105 such that a major thickness axis is oriented parallel to the belt surface 142. In other words, the leveling device 410 creates a single layer of articles 105 on the conveyor belt 140 by re-orienting leaning, stacked or other non-conforming articles 105 to form a single layer. The paddles 422 may be formed of a complaint or soft material, such as but not limited to rubber, fabric or polymeric material so as to not damage the articles 105. This may be particularly important when the articles 105 are still warm or hot from manufacturing and may be easily damaged. The conveyor belt 140 then transports the articles to an article inspection station 500.

Referring again to FIGS. 1-4, the inspection station 500 includes at least one automated device 510. In this exemplary embodiment, the automated device 510 is a vision guided robot configured to identify and remove articles 105 determined to be defective and being transported through the inspection station 500 by the conveyor belt 140. In another embodiment, the automated device 510 may include vision and pick and place devices capable of identifying and moving articles 105 within the apparatus 100. The vision guided robot includes software and hardware capable of identifying articles 105 which are determined to be outside of one or more acceptable design criteria, or in other words, defective. The vision guided robot further includes a removal device 511 for removing defective articles 105 from the conveyor belt 140. In this exemplary embodiment, the removal device 511 is a vacuum pad or nozzle that is brought in contact with an article 105 so as to temporarily attach to the article 105, thereby allowing the article 105 to be lifted from or otherwise removed from the conveyor belt 140. In another embodiment, the removal device 511 may be a mechanical gripper or other attachment device. The automated device 510 then places any removed articles onto a defective article chute 520 (see particularly FIG. 4 for an articles 105 placed on the chute 520) for removal from the apparatus 100. Removed articles 105 may then be collected and/or recycled for further processing.

In addition to removing articles 105 determined to be defective from the conveyor belt 140, the automated device 510 further selects articles determined to meet acceptable design criteria and similarly removes the acceptable articles 105 from the conveyor belt 140, such as with removal device 511. The acceptable articles 105 are placed in a predetermined oriented position on a discharge conveyance device 540. The automated device 510 further includes software and hardware configured to determine acceptable design criteria and place the acceptable articles 105 in a predetermined orientation upon the discharge conveyance device 540. The discharge conveyance device 540 includes a conveyor belt 542 having an upward facing belt surface 544 and a drive (not shown) for causing the conveyor belt 542 to move. The conveyor belt 542 includes perforations 546.

Referring again to FIGS. 1-4, the apparatus 100 further includes an air vacuum device 143 configured to draw air through perforations 546 in the belt surface 544. The air vacuum device 143 includes a vacuum blower 145 and various conduits, ducting, and vacuum flow devices (not shown) configured to apply a vacuum to a bottom surface (not shown)

of the conveyor belt 542. The drawn air creates an object-stabilizing suction force on articles 105 located on the belt surface 544 when the conveyor belt 542 moves relative to the air vacuum device 143. In one embodiment, the conveyance device 100 may include a control (not shown) for changing the suction force imposed on the articles 105 while being transported on the belt surface 544. In another embodiment, the discharge conveyance device 540 may be a conveyor belt, mat top conveyor, roller conveyor, cable conveyor, table top chain conveyor or other similar article transport device.

Figure 7:
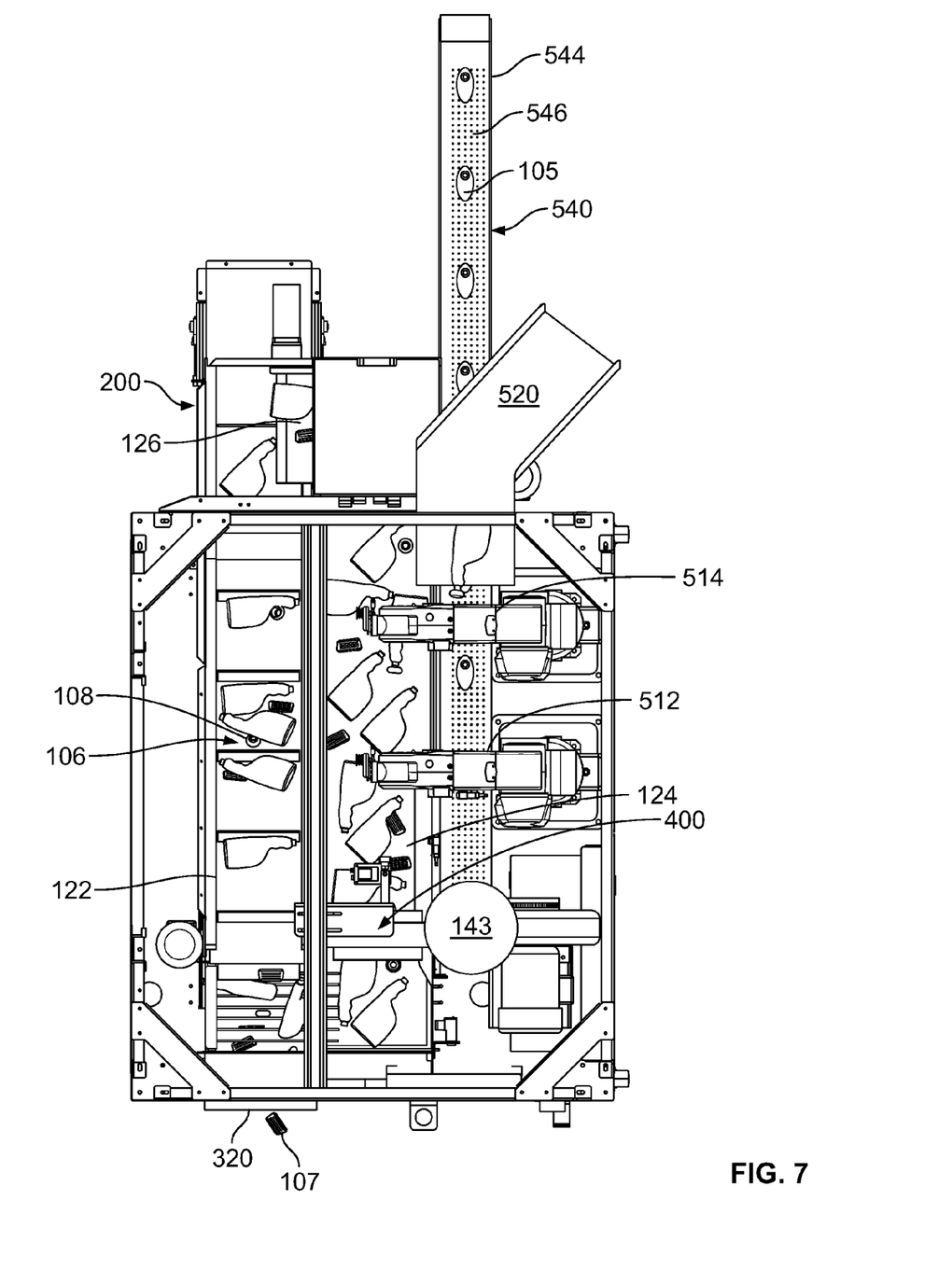
FIG. 7 illustrates a top view of an embodiment and inspection and orienting apparatus according to another embodiment of the disclosure.
Figure 8:
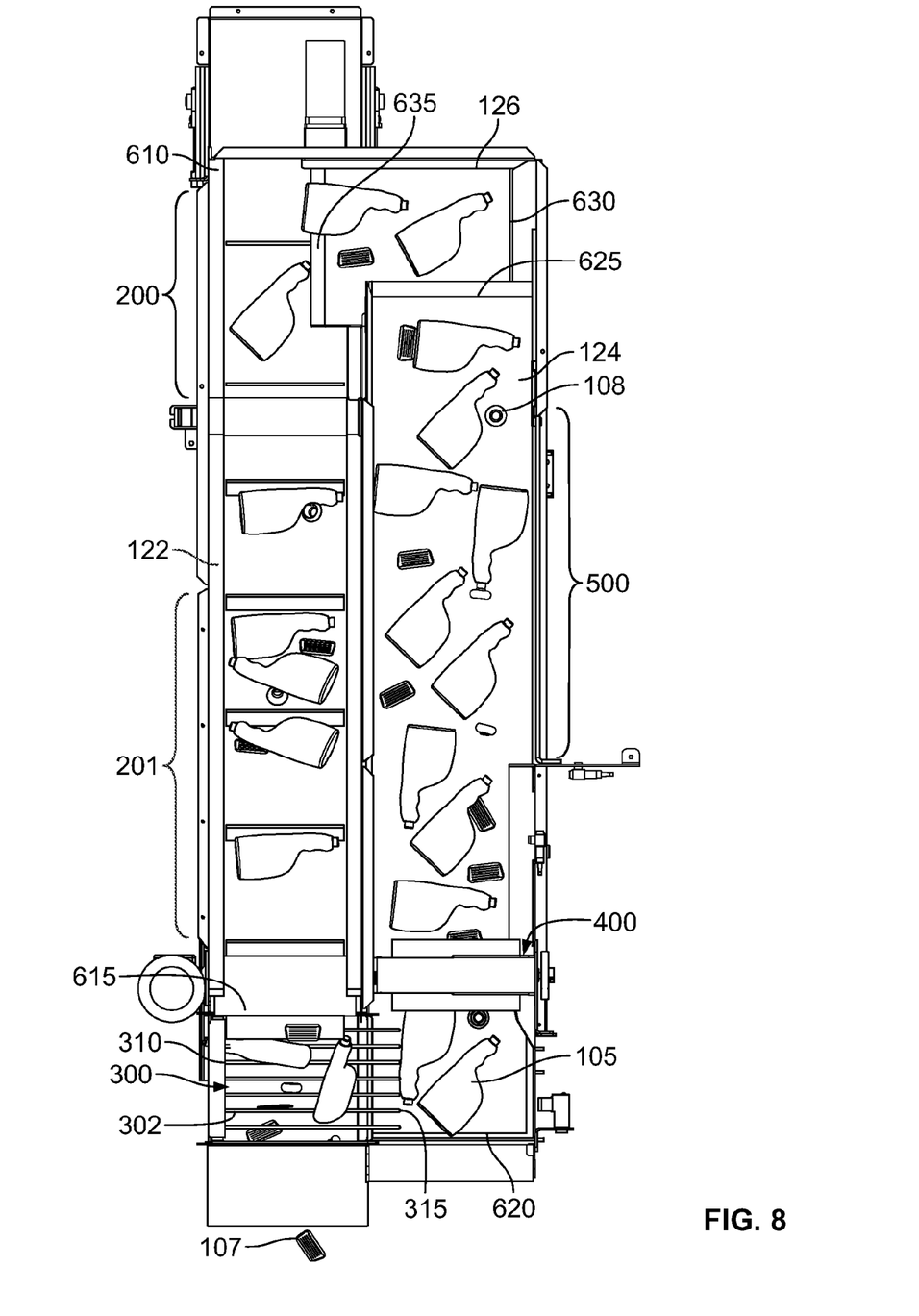
FIG. 8 illustrates a simplified top view of the inspection and orienting apparatus of FIG. 1.

FIG. 7 illustrates another exemplary embodiment of the apparatus 100. As can be seen in FIG. 7, the inspection station 500 includes a first automated device 512 and a second automated device 514. The first automated device 512 is configured to determine those articles 105 that meet acceptable design criteria, remove those articles 105 from the conveyor belt 542, and place those articles 105 in a predetermined orientation upon the discharge conveyance device 540. The second automated device 514 is configured to determine those articles 105 that do not meet acceptable design criteria or in other words are defective, remove those articles 105 from the conveyor belt 542, and place those articles on defective article chute 520 for removal from the apparatus 100. In another embodiment, the inspection station 500 may include one or more automated devices 514.

Referring to FIGS. 2-4 and 8, the articles 105, after passing through the inspection station 500, are transported by the second section 124 to the third section 126 for return to the first section 122. The third section 126 may a cross-feed belt conveyor. In another embodiment, the third section 126 may be a belt conveyor, roller conveyor, mat conveyor, chute or slide or other similar article transport device. In one embodiment, the third section 124 may be of a narrow conveyor belt width compared to the second section 124 in order to facilitate the transport of the articles 105 from the second section 124 to the first section 122. In such a manner, articles 105 and manufacturing waste 106 not removed by the apparatus 100 are recycled through the article receiving station 200, the waste separation station 300, the article leveling station 400, and the inspection station 500. The recycling of the articles 105 and manufacturing waste 106 allows for the additional opportunities for manufacturing waste 106 and articles 105 determined to be defective to be removed, as well as articles 105 deemed to be acceptable to be oriented. This is accomplished by the repositioning and/or re-orienting of the articles 105 and manufacturing waste 106 during recirculation process.

Figure 1:
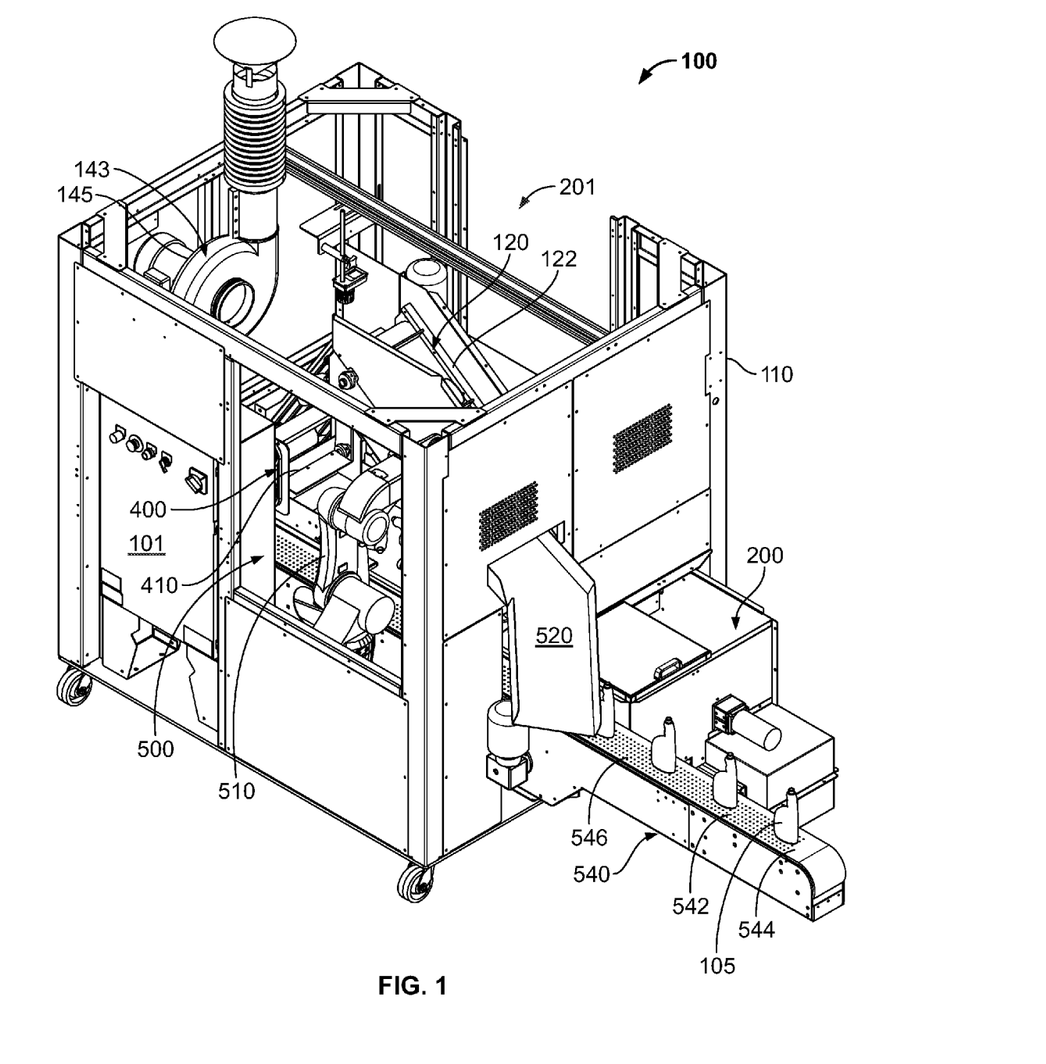
FIG. 1 illustrates a perspective view of an inspection and orienting apparatus according to an embodiment of the disclosure.
Figure 2:
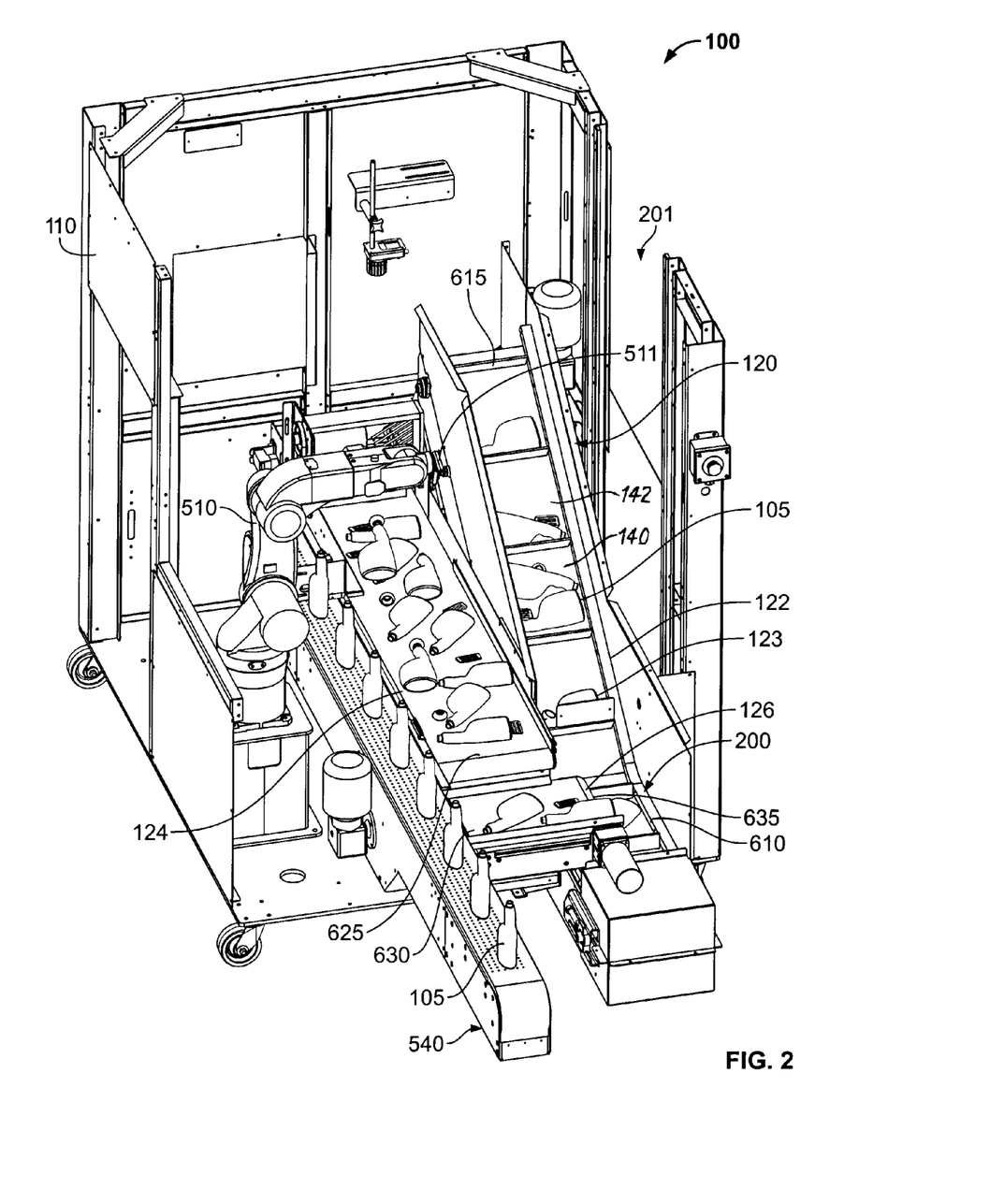
FIG. 2 illustrates a partial cutaway, perspective view of the inspection and orienting apparatus of FIG. 1.
Figure 3:
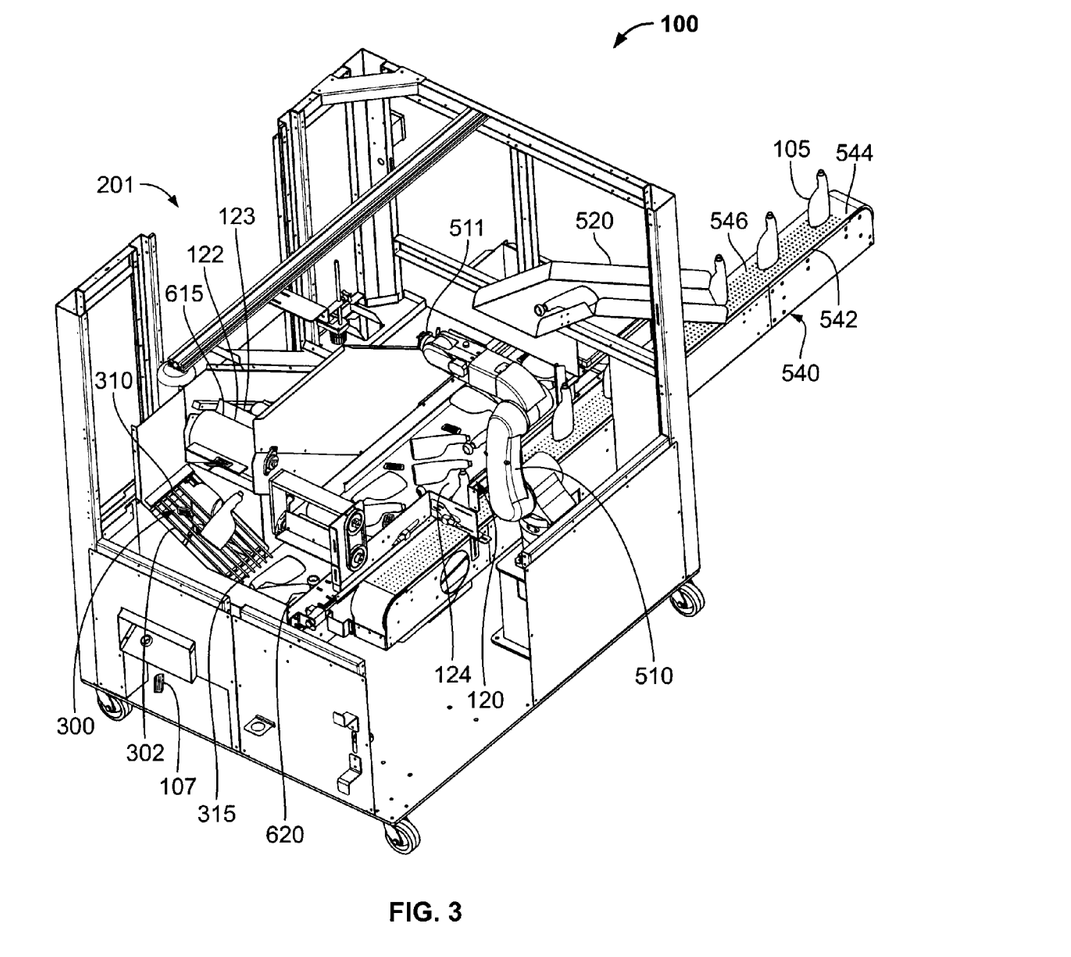
FIG. 3 illustrates another partial cutaway, perspective view of the inspection and orienting apparatus of FIG. 1.
Figure 4:
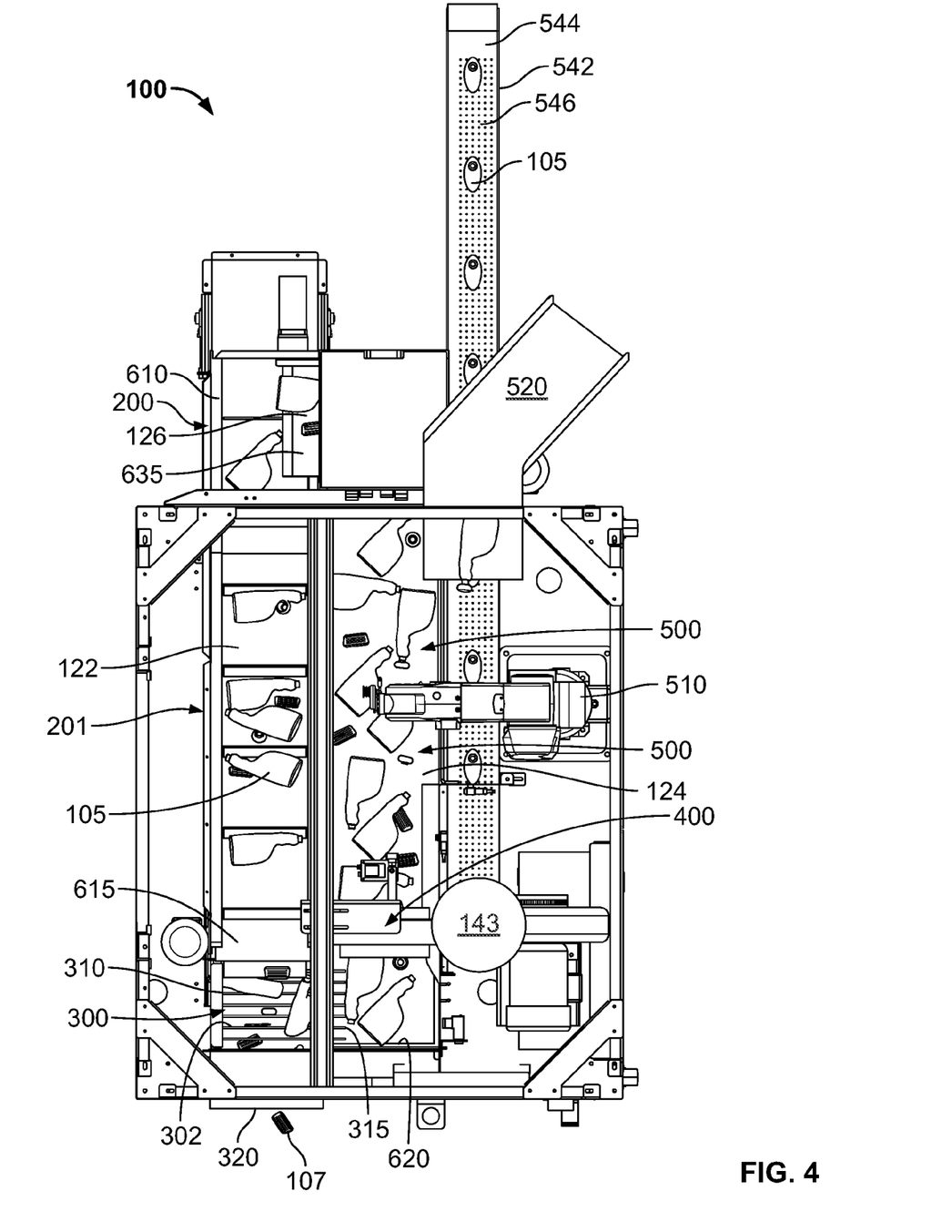
FIG. 4 illustrates a top view of the inspection and orienting apparatus of FIG. 1.

Referring to FIG. 1, the apparatus 100 further includes a control system 101 to operate the various components of the apparatus, including, but not limited to the operation of the conveyance device 120, at least one automated devices 510, the article leveling device 410, and the air vacuum device 143. The control system 101 may include any number of manual and automated systems for performing the apparatus functions.

Referring to FIGS. 2, 3, 4 and 8, the conveyance device 120 includes sections that are inclined and/or at different horizontal levels or heights. In this exemplary embodiment, the first section 122 is inclined upward from an initial position 610 below the third section 126 to a final position 615 above the waste separation station 300. The waste separation station 300 is inclined downward from an initial position 310 below the first section 122 to a final position 315 proximate the second section 124. The second section 124 is approximately level and extends from an initial position 620 proximate the final position 315 of the separation station 300 to a final position 625 above the third section 126. The third section 126 extends approximately level from an initial position 630 below the final position 625 of the second section 124 to a final position 635 above the initial section 610 of the first section 122. In such a manner, the conveyance device 120 and separation station 300 form a continuous loop that recirculates articles 105 through the apparatus 100 to re-orients and/or repositions articles and manufacturing waste 106 to be further separated and/or identified and/or classified as acceptable or defective. In another embodiment, any one or combination of the sections and/or separation station 300 may be at the same or different heights and/or inclinations.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An apparatus, comprising:
an article receiving station;
an inspection station, the article receiving station and the inspection station forming a continuous loop; and
a conveyance device for transporting articles between the article receiving station and the inspection station;
the inspection station includes one or more automated devices for removing defective articles and orienting acceptable articles from the conveyance device;
wherein the conveyance device recirculates articles not removed from the inspection station back to the article receiving station.

2. The apparatus of claim 1, further comprising:
an article leveling station.

3. The apparatus of claim 1, further comprising:
a waste separation station.

4. The apparatus of claim 1, wherein the waste separation station comprises an open bar grid configured to separate manufacturing waste from the articles.

5. The apparatus of claim 1, where the one or more automated devices comprises one or more vision guided robots.

6. The apparatus of claim 1, further comprising:
a discharge conveyance device for removing oriented articles from the apparatus.

7. The apparatus of claim 1, wherein the inspection station comprises a first automated device for removing defective articles from the apparatus and a second automated device for orienting acceptable articles from the conveyance device.

8. An article inspecting and orienting apparatus, comprising:
an article receiving station;
a waste separation station;
an article leveling station;
an inspection station, the article receiving station and the inspection station forming a continuous loop; and
a conveyance device for transporting articles between the article receiving station, the waste separation station, and the inspection station;
the inspection station includes one or more automated devices for removing defective articles and orienting acceptable articles from the conveyance device;

wherein the conveyance device recirculates articles not removed from inspection station back to the article receiving station.

9. The apparatus of claim 8, wherein the articles are blow-molded containers.

10. The apparatus of claim 8, wherein the waste separation station comprises an open bar grid configured to separate manufacturing waste from the articles.

11. The apparatus of claim 8, where the one or more automated devices comprises one or more vision guided robots.

12. The apparatus of claim 8, further comprising:
a discharge conveyance device for removing oriented articles from the apparatus.

13. The apparatus of claim 8, wherein the inspection station comprises a first automated device for removing defective articles from the apparatus and a second automated device for orienting acceptable articles from the conveyance device.

14. A method of inspecting and orienting a plurality of articles, comprising:
receiving a plurality of articles from a manufacturing process at a receiving station;
separating manufacturing waste from the plurality of articles;
providing the plurality of articles to an inspection station, the receiving station and the inspection station forming a continuous loop;
inspecting the received plurality of articles;
removing defective articles from the plurality of articles that fail inspection;
orienting acceptable articles from the plurality of articles that pass inspection; and
recirculating remaining articles that pass through the inspection station to the receiving station.

15. The method of claim 14, wherein the plurality of articles are blow-molded containers.

16. The method of claim 14, wherein the inspection station uses one or more automated devices to inspect and orient the plurality of articles.

17. The method of claim 14, wherein the manufacturing waste is separated from the plurality of articles by an open bar grid.

18. The method of claim 14, further comprising:
leveling the plurality of articles prior to inspection.

19. The method of claim 14, wherein the plurality of articles are inspected by at least one vision guided robot.

* * * * *